US010485950B2

(12) United States Patent
Elia et al.

(10) Patent No.: US 10,485,950 B2
(45) Date of Patent: Nov. 26, 2019

(54) MULTIPURPOSE CABLING

(71) Applicant: ART Medical Ltd., Netanya (IL)

(72) Inventors: Liron Elia, Kiryat-Ata (IL); Gavriel J. Iddan, Haifa (IL)

(73) Assignee: ART Medical Ltd., Netanya (IL)

( * ) Notice: Subject to any disclaimer, the term of this patent is extended or adjusted under 35 U.S.C. 154(b) by 0 days.

(21) Appl. No.: 15/878,435

(22) Filed: Jan. 24, 2018

(65) Prior Publication Data

US 2019/0038868 A1 Feb. 7, 2019

Related U.S. Application Data

(60) Provisional application No. 62/540,603, filed on Aug. 3, 2017.

(51) Int. Cl.
*A61B 1/005* (2006.01)
*A61B 1/015* (2006.01)
(Continued)

(52) U.S. Cl.
CPC ..... *A61M 25/0074* (2013.01); *A61B 1/00018* (2013.01); *A61B 1/00027* (2013.01); *A61B 1/0052* (2013.01); *A61B 1/0057* (2013.01); *A61B 1/00114* (2013.01); *A61B 1/012* (2013.01); *A61B 1/015* (2013.01); *A61M 25/0097* (2013.01); *A61J 15/00* (2013.01);
(Continued)

(58) Field of Classification Search
CPC ... A61B 1/01; A61B 1/00018; A61B 1/00112; A61B 1/0057; A61B 1/0055; A61B 1/012; A61B 1/015; A61B 2017/00323; A61M 2025/015; G02B 23/2484
See application file for complete search history.

(56) References Cited

U.S. PATENT DOCUMENTS

| 4,301,790 A | * | 11/1981 | Bol | A61B 1/00018 348/65 |
| 4,519,391 A | * | 5/1985 | Murakoshi | A61B 1/05 348/E5.043 |

(Continued)

OTHER PUBLICATIONS

Invitation to Pay Additional Fees, Communication Relating to the Results of the Partial International Search and the Provisional Opinion dated Nov. 12, 2018 From the International Searching Authority Re. Application No. PCT/IL2018/050847. (16 Pages).

(Continued)

*Primary Examiner* — John P Leubecker

(57) ABSTRACT

A catheter, comprising: a flexible tubular member having at least one lumen therethrough and a proximal end and a distal end; a plurality of conductive cables extending through at least one of the at least one lumen; and at least one electrically operated component, attached at the distal end and powered by at least one electrical current driven on at least one of the plurality of conductive cables. Some of the plurality of conductive cables are attached to the distal end such that the flexible tubular member is deformed by exerting at the proximal end a tensile force on one of the some of the plurality of conductive cables and a compressive force on another of the some of the plurality of conductive cables, while the at least one electrical current is driven on the some of the plurality of conductive cables.

24 Claims, 16 Drawing Sheets

(51) Int. Cl.
  *A61M 25/00* (2006.01)
  *A61B 1/012* (2006.01)
  *A61B 1/00* (2006.01)
  *A61M 25/01* (2006.01)
  *A61J 15/00* (2006.01)

(52) U.S. Cl.
  CPC ..... *A61M 25/0029* (2013.01); *A61M 25/0138* (2013.01); *A61M 25/0147* (2013.01); *A61M 25/0158* (2013.01); *A61M 2025/0161* (2013.01)

(56) References Cited

U.S. PATENT DOCUMENTS

| | | | | |
|---|---|---|---|---|
| 5,228,430 A | * | 7/1993 | Sakamoto | A61B 1/05 348/65 |
| 5,413,107 A | | 5/1995 | Oakley et al. | |
| 5,685,823 A | * | 11/1997 | Ito | A61B 1/00091 600/121 |
| 5,827,272 A | * | 10/1998 | Breining | A61B 5/0422 606/41 |
| 7,369,901 B1 | * | 5/2008 | Morgan | A61N 1/059 600/375 |
| 7,725,161 B2 | * | 5/2010 | Karmarkar | G01R 33/287 600/423 |
| 2006/0041188 A1 | * | 2/2006 | Dirusso | A61B 1/0055 600/146 |
| 2006/0200000 A1 | * | 9/2006 | Sato | A61B 1/0055 600/146 |
| 2007/0043261 A1 | * | 2/2007 | Watanabe | A61B 1/00071 600/144 |
| 2008/0194911 A1 | * | 8/2008 | Lee | A61B 1/0055 600/109 |
| 2009/0163769 A1 | * | 6/2009 | Robertson | A61B 1/0014 600/109 |
| 2013/0066297 A1 | * | 3/2013 | Shtul | A61B 1/015 604/514 |
| 2013/0112457 A1 | * | 5/2013 | Kitagawa | A61B 1/0056 174/68.3 |
| 2016/0030707 A1 | * | 2/2016 | Dillon | A61B 1/00119 600/156 |
| 2017/0127915 A1 | * | 5/2017 | Viebach | A61B 1/00011 |

OTHER PUBLICATIONS

International Search Report and the Written Opinion dated Jan. 9, 2019 From the International Searching Authority Re. Application No. PCT/IL2018/050847. (22 Pages).

* cited by examiner

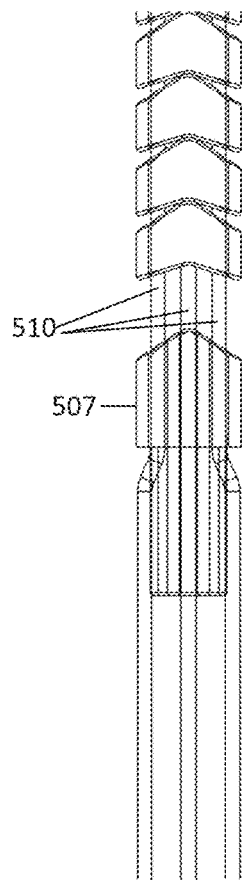
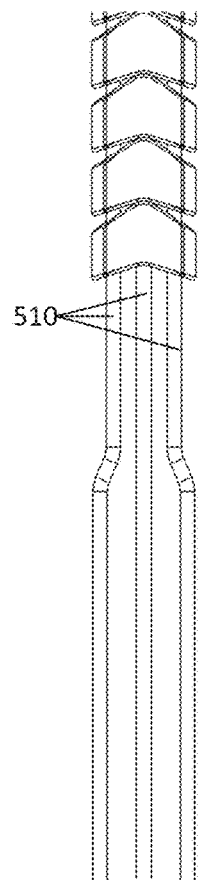
FIG. 9A  FIG. 9B
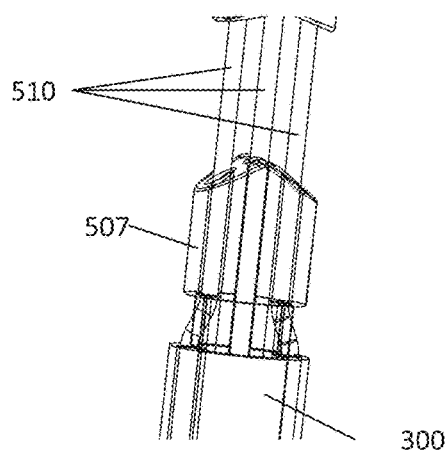
FIG. 9C

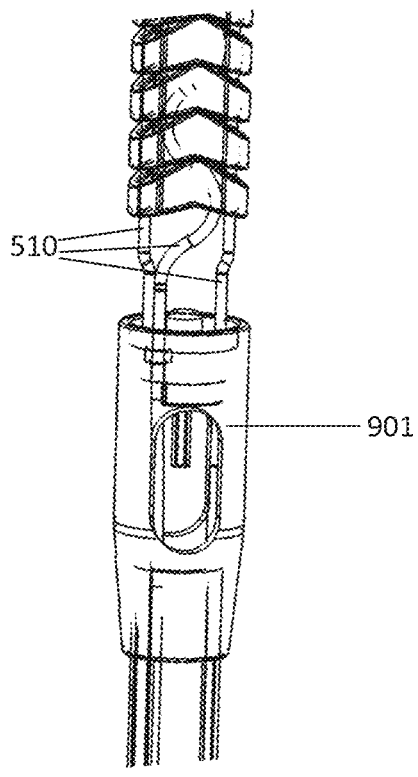
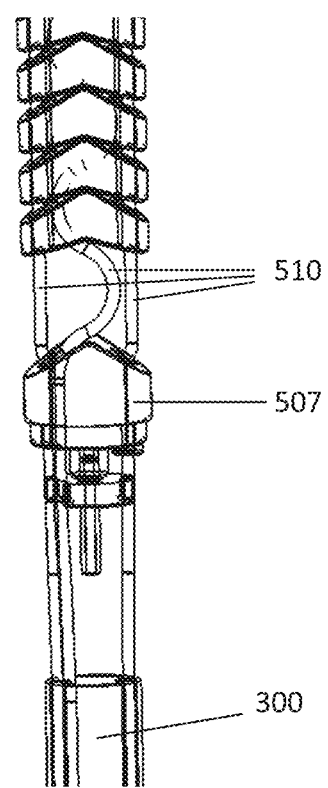
FIG. 10A
FIG. 10B

MULTIPURPOSE CABLING

RELATED APPLICATIONS

The U.S. patent application Ser. No. 15/878,435 claims the benefit of priority under 35 USC § 119(e) of U.S. Provisional Patent Application No. 62/540,603, filed on Aug. 3, 2017, the contents of the which are all incorporated by reference as if fully set forth herein in their entirety.

BACKGROUND

The present invention, in some embodiments thereof, relates to a multipurpose tube and, more specifically, but not exclusively, to a catheter used in a medical environment.

In a medical environment there may be a need to operate an electrical component, for example a camera, at a target location in a patient's body. Operating such a component may include delivering an electrical current to the component, and optionally delivering force or motion to move the component. For example, an electrical current may be required for powering a camera and an illumination component adjacent to the camera, and force or motion may be required to move the camera and point the camera's lens in multiple directions. Typically, a catheter, that is a tube having an elongated form and one or more lumens extending therethrough, is used to encase the electrical component, one or more wires for delivering motion, and one or more electrical wires for delivering electrical current to the electrical component.

In some medical environments there may be a need to simultaneously deliver or remove one or more fluids to or from the target location. Simultaneously delivering a fluid and an electrical current typically require separating electrical wires from a lumen delivering a fluid to avoid electrical short circuits.

SUMMARY

It is an object of the present invention to provide a device for simultaneously delivering two or more of force, motion, electricity and fluids from a command location near a patient's body to a target location in the patient's body while maintaining minimal dimensions. The approach is advantageous when space is limited and there is a need for a multipurpose device, for example when performing an endoscopy, a laparoscopy, or another intra-body procedure in an organ which is limited in space.

The design embodiment intended for an endoscope, shown later in more details and in figures, proposes the use of coatings for insulation when a hollow wire is used for simultaneous delivery of fluids and electricity. In addition, terminations on a proximal end (operator side) of the device and a distal end (patient side) of the device are shown in the figures.

The foregoing and other objects are achieved by the features of the independent claims. Further implementation forms are apparent from the dependent claims, the description and the figures.

According to a first aspect of the invention, a catheter comprises: a flexible tubular member having at least one lumen therethrough and a proximal end and a distal end; a plurality of conductive cables extending through at least one of the at least one lumen; and at least one electrically operated component, attached at the distal end and powered by at least one electrical current driven on at least one of the plurality of conductive cables. Some of the plurality of conductive cables are attached to the distal end such that the flexible tubular member is deformed by exerting at the proximal end a tensile force on one of the some of the plurality of conductive cables and a compressive force on another of the some of the plurality of conductive cables, while the at least one electrical current is driven on the some of the plurality of conductive cables. Using multipurpose cables for delivering force and electrical current and signals allows reducing a diameter of a catheter.

According to a second aspect of the invention, a catheter comprises: a flexible tubular member having at least one lumen therethrough and a proximal end and a distal end; a plurality of hollow conductive cables, extending through the at least one lumen and each having a cable lumen therethrough; and at least one electrically operated component, attached at the distal end and powered by at least one electrical current driven on at least one of the plurality of hollow conductive cables. The cable lumen is coated in an insulating material such that the electrically operated component is powered by the at least one electrical current while a fluid is transferred through the cable lumen of the at least one of the plurality of hollow conductive cables. Using multipurpose cables for delivering a fluid and electrical current and signals allows reducing a diameter of a catheter.

With reference to the first aspect, in a first possible implementation of the first aspect of the present invention at least one of the plurality of conductive cables is coated in an insulating material such that the electrically operated component is powered by the at least one electrical current while a fluid is transferred through the at least one lumen. Using an insulating coating prevents the fluid from interfering with the at least one electrical current.

With reference to the first aspect, or the first possible implementation of the first aspect of the present invention, in a second possible implementation of the first aspect of the present invention the at least one lumen has an outlet at the distal end. The outlet allows delivering a fluid to a location inside a patient's body, from outside the patient's body.

With reference to the first aspect, in a third possible implementation of the first aspect of the present invention the at least one electrically operated component comprises a camera or an illumination component. Optionally, the illumination device is a light emitting diode in the ultra-violet, visible or infra-red spectrum (VLED), powered by the at least one electrical current. Optionally, the at least one electrically operated component comprises a printed circuit board (PCB) having an elongated form, fitting inside the flexible tubular member. A camera and illumination allow delivering the catheter without the use of additional scanning equipment external to the patient's body.

With reference to the first aspect, in a fourth possible implementation of the first aspect of the present invention the flexible tubular member comprises at the distal end a sequence of ring segments having a virtual shaft, such that the flexible tubular member has at least one degree of bending freedom. At least one degree of bending freedom allows controlling the electrically operated component's orientation inside the patient's body.

With reference to the first aspect, in a fifth possible implementation of the first aspect of the present invention some of the plurality of conductive cables are attached to the distal end by a mechanical coupling selected from a group consisting of a crimp connection, a welding, a bonding and a soldering. Some of the plurality of conductive cables are electrically attached to the at least one electrically operated component using at least one length of flexible conducting wire. Optionally, the at least one length of flexible conducting wire has a length of between 3 and 20 millimeters. A flexible wire allows exerting force on the some of the plurality of conductive cables without disrupting an attachment between the some of the plurality of conductive cables and the distal end. Optionally, the mechanical coupling is reinforced by a bonding agent at one or more points of contact between the plurality of conductive cables and the flexible tubular member.

With reference to the first aspect or the fifth possible implementation of the present invention, in a sixth possible implementation of the first aspect of the present invention the flexible tubular member comprises at the distal end a sequence of ring segments having a virtual shaft. The at least one point of contact is between the plurality of conductive cables and at least one of the sequence of ring segments. Optionally, a diameter of at least one of the sequence of ring segments is narrower than a diameter of the flexible tubular member at a proximal end of the flexible tubular member. Optionally, a diameter of at least one of the sequence of ring segments is wider than a diameter of the flexible tubular member at a proximal end of the flexible tubular member. Different shapes of the distal end are suitable for using the catheter in various organs.

With reference to the first aspect, in a seventh possible implementation of the first aspect of the present invention the catheter further comprises a pulley or capstan at the proximal side. Some of the plurality of conductive cables are connected to the pulley or capstan, such that a motion of the pulley or capstan exerts at the proximal end a tensile force on at least one of the some of said plurality of conductive cables and a compressive force on at least one other of the some of said plurality of conductive cables.

With reference to the first aspect, in an eighth possible implementation of the first aspect of the present invention the at least one of the at least one electrical current is either a direct current (DC) or an alternating current (AC). Some electrically operated components require a direct current, other electrically operated components require an alternating current.

With reference to the first aspect, in a ninth possible implementation of the first aspect of the present invention the at least one first of said plurality of conductive cables delivers a plurality of electrical signals from the at least one electrically operated component to a receiver electrically attached to the at least one of said plurality of conductive cables. The at least one first conductive cable extends through a first of the at least one lumen. The at least one second of the plurality of conductive cables delivers an electrical current to a first of the at least one electrically operated component and extends through a second of the at least one lumen. The at least one third of the plurality of conductive cables delivers an electrical current to a second of the at least one electrically operated component and extends through a third of the at least one lumen. The first lumen is between the second lumen and the third lumen. Electrical signals may be delivered from the electrically operated component to a receiver, for example a plurality of video images. Separating the plurality of conductive cables between a plurality of lumens reduces electrical interferences between the plurality of conductive cables.

With reference to the first aspect, in a tenth possible implementation of the first aspect of the present invention the catheter further comprises at least one electrical signal modulator attached to the some of the plurality of conductive cables on a proximal or distal end and at least one electrical signal demodulator attached to the some of the plurality of conductive cables on an opposite end, for the purpose of delivering a plurality of electrical signals on the some of the plurality of conductive cables.

With reference to the first aspect, in an eleventh possible implementation of the first aspect of the present invention the sequence of ring segments comprises a plurality of sections, each comprising a sub-sequence of rings, each ring having a certain section ring cylinder height. A first section is closer to a proximal end of the flexible tubular member than a second section, and a first section ring cylinder height of the sub-sequence of rings of the first section is greater than a second ring cylinder height of the sub-sequence of rings of the second section, such that a bending radius of the first section is greater than a bending radius of the second section. Having a plurality of sections having a plurality of bending radii may allow greater flexibility in deforming the catheter and allow easier insertion in hard to access organs. Optionally, the sequence of ring segments comprises two sections, the first ring cylinder height is greater than 2 millimeters and up to 5 millimeters, and the second cylinder ring height is less than 2 millimeters.

With reference to the first aspect, in a twelfth possible implementation of the first aspect of the present invention at least one of the plurality of conductive cables is installed in a spiral tubular member having a plurality of coils. The spiral tubular member extends through at least part of one of the at least one lumen. Optionally, the spiral tubular member comprises a wire having a diameter between 0.05 millimeters and 0.5 millimeters, and the wire is coiled between 5 and 100 coils per centimeter.

With reference to the second aspect, in a first possible implementation of the second aspect of the present invention the cable lumen has an outlet at the distal end.

With reference to the second aspect, in a second possible implementation of the second aspect of the present invention some of the plurality of hollow conductive cables are attached to the distal end such that the flexible tubular member is deformed by exerting at the proximal end a tensile force on one of the some of the plurality of hollow conductive cables and a compressive force on another of the some of the plurality of hollow conductive cables, while the fluid is transferred through the cable lumen.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A, 9B and 9C are additional schematic illustrations of the multi-lumen member shown in FIGS. 6, 7 and 8, emphasizing a narrowing form, according to some embodiments of the present invention;

FIGS. 10A and 10B are additional schematic illustrations of the multi-lumen member shown in FIGS. 6, 7 and 8, emphasizing a widening form, according to some embodiments of the present invention;

DETAILED DESCRIPTION

Figure 1:
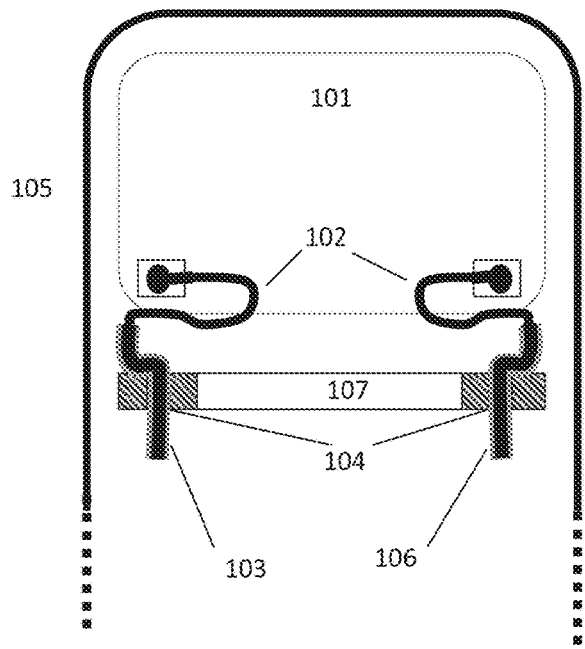
FIG. 1 is a schematic partial illustration of an exemplary catheter according to some embodiments of the present invention, using a common wire for delivering a force and an electrical current.

The present invention, in some embodiments thereof, relates to a medical tube and, more specifically, but not exclusively, to a catheter used in a medical environment, optionally for feeding. The present invention benefits other applications for limited available space, for example laparoscopy and robotic arms, where using multifunction elements of the present invention promotes reduction in dimensions of a device used in such applications. A reduced sized device is easier to insert and reduces the patient's trauma.

In a medical environment there may be a need for a device to simultaneously deliver force, motion, electrical current and fluids from a command location near a patient's body to a target location in the patient's body, for instance for post pyloric feeding and inserting a robotic arm. Such a device is typically sized and shaped as a compact elongated form, having one or more lumens extending therethrough. Enteral feeding is a method of nutritional support in patients who have a functioning gastrointestinal tract but cannot maintain an adequate oral intake. The enteral route traditionally delivers nutrition directly into the patient's stomach via a nasogastric tube or gastrostomy (pre pyloric feeding). Post pyloric feeding is a method of delivering nutrition directly into the small bowel. There exist medical indications preferring post pyloric feeding to pre pyloric feeding. Some common techniques of placing a tube for post pyloric feeding require skilled radiological support and expose the patient and medical personnel to radiation in order to correctly deliver a distal end of a feeding tube to a target location. Alternately, in addition to the feeding tube, a camera may be delivered to the target location (for example by an endoscope) to provide a plurality of still images or a video stream to assist the medical personnel in correctly placing the feeding tube.

Simultaneously delivering a fluid and an electrical power to a device such as a camera typically requires separating electrical wires from a lumen delivering a fluid to avoid electrical short circuits. Typically, separate catheters are used for delivering fluids and for carrying an electrical component and one or more wires for delivering an electrical current to the electrical component, allowing simultaneous use only in organs, wide enough to accommodate the separate catheters simultaneously. Typically, it is desired for a medical catheter to have as small as possible a diameter to ease insertion and to minimize associated trauma to the patient's body. It would therefore be highly advantageous to functionally and physically combine the needed activities into a single multipurpose entity.

Henceforth, the terms "wire" and "cable" are used interchangeably and mean a metal strand, metal cord, a capillary or a hollow wire.

The present invention, in some embodiments thereof, enables designing a compact device for simultaneously delivering force, motion, electrical current, electrical signals and fluids by using one or more multipurpose conductive wires in a single catheter having a tubular member. Optionally, the tubular member has one or more lumens therethrough. Optionally, the multipurpose conductive wires deliver both electrical current and signals and motion to an electrically operated component attached to a distal end of the tubular member. In some embodiments the multipurpose conductive wires are coated in an insulating material such that a fluid, for example a nutritional fluid, may be delivered through at least one of the lumens while delivering an electrical current to the electrically operated component.

Optionally, one or more of the multipurpose conductive wires are hollow, having a wire lumen extending therethrough. Optionally, the wire lumen is coated in an insulating material, for example Parylene, allowing a fluid to be delivered through the wire lumen while an electrical current and electrical signals are delivered on at least one of the one or more multipurpose conductive wires.

A device designed using the present invention may be designed to have a form small enough to fit in small organs, too small to accommodate more than one catheter simultaneously, extending the range of possible medical procedures. For example, the present invention enables reducing exposure to radiation in positioning a post pyloric feeding tube by using a camera inserted in the same catheter as the post pyloric feeding tube to assist in positioning the post pyloric feeding tube. Using a single wire for delivering fluid, electrical current and force and motion further reduces a diameter of the tubular member required to encase the one or more multipurpose conductive wires, allowing access by such a device to even smaller organs than other catheters allow.

In some embodiments of the present invention the distal end of the tubular member comprises a sequence of ring segments having a virtual shaft, providing flexibility to the tubular member. Optionally, the sequence of ring segments comprises two or more sections of segments having a uniform cylinder height. The term "cylinder height" as used herein means a dimension of a segment parallel to the tubular member's length and perpendicular to the segment's circumference. For brevity, the term "height" is used to mean "cylinder height". Segments in one section may have a uniform height different from a uniform height of segments in a second section. Each segment has a bending radius, with a first section comprising a first sequence of rings having a first uniform height having a greater bending radius than a bending radius of a second section comprising a second sequence of rings having a second uniform height less than the first uniform height. Having sections with different bending radii allows more accuracy in manipulating a position of an electrical component at the distal end of the tubular member.

In addition, in some embodiments of the present invention, at least one of the plurality of multipurpose conductive wires is installed inside a spiral tubular cover, or sheath, having a plurality of coils and extending through at least part of one of the tubular member's one or more lumens. Using a coiled sheath, that is a spring, may reduce friction between the at least one multipurpose conductive wire and the tubular member.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, showing a schematic partial illustration of an exemplary catheter according to some embodiments of the present invention, using a multipurpose wire for delivering a force and an electrical current. In such embodiments, a flexible tubular member 105 having one or more lumens therethrough encases at least one electrically operated component 101 at a distal end of the flexible tubular member. In such embodiments, the distal end of the tubular member is delivered to a location inside a patient's body, and a proximal end of the tubular member remains at a command location outside the patient's body. Optionally, the at least one electrically operated component is an imager, for instance a camera or any other radiation capturing component. Optionally, the at least one electrically operated component is an illumination component, for example a Light Emitting Diode (LED). The LED may emit light in the visible, ultra-violet (UV) or infra-red (IR) spectrum (that is, the LED is a VLED). Optionally, the at least one electrically operated component is powered by an electrical current driven on one or more of a plurality of multipurpose conductive cables 103 and 106, extending through at least one of the one or more lumens. The at least one electrically operated component may be powered by a direct current (DC) delivered on one of the plurality of multipurpose conductive cables. Optionally, the at least one electrically operated component is powered by an alternative current (AC) delivered on one of the plurality of multipurpose conductive cables. The one or more multipurpose conductive cables 103 and 106 may be mechanically attached to the distal end of member 105. For example, the one or more multipurpose conductive cables may be welded to the distal end of member 105. Electrically operated component 101 may be mounted at member 105's distal end on a printed circuit board (PCB) having one or more fixing elements, for example a crimp connection, a welding or micro-welding, a bonding, a soldering or nuts and bolts, and the one or more multipurpose conductive cables may be attached to member 105 using the PCB's fixing elements. In some embodiments the PCB has an elongated form, fitting in the distal end of tubular member 105. Optionally, the distal end of the flexible tubular member comprises at least one ring segment 107, and the one or more multipurpose conductive cables 103 and 106 are mechanically attached to segment 107 at points 104 for the purpose of bending the flexible tubular member and allowing motion of the flexible tubular member by exerting force on multipurpose conductive cables 103 and 106. One or more of points 104 may be reinforced by a bonding agent, for example a high strength epoxy. Optionally, one or more flexible conducting wires 102 may be used to attach electrically operated component 101 to the one or more multipurpose conductive cables 103 and 106. In such embodiments, the one or more flexible conducting wires 102 deliver at least one electrical current from cables 103 and 106 to the electrically operated component 101, for the purpose of powering and controlling component 101.

There may be a need to tilt the electrically operated component, for example to point a camera at more than one possible direction.

Figure 2:
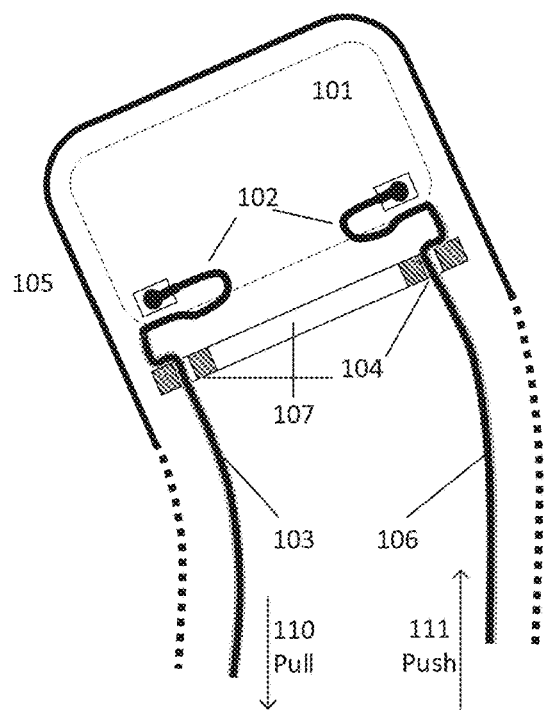
FIG. 2 is another schematic partial illustration of the exemplary catheter shown in FIG. 1.

Reference is now also made to FIG. 2, showing another schematic partial illustration of the exemplary catheter shown in FIG. 1, according to some embodiments of the present invention. In such embodiments, when as tensile force 110 (pull) is exerted on cable 103 and a compressive force 111 (push) is exerted on cable 106, the flexible member 105 is deformed. For example, the flexible member may bend towards the direction of tensile force 110. This deformation may tilt the at least one electrically operated component. Optionally, a pulley, or a capstan, is attached to wires 103 and 106 at the proximal side of the tubular member, and a motion of the pulley or capstan exerts the tensile force and compressive force. Optionally, an electrical current is driven through one or more of cables 103 and 106 while the compressive force and the tensile force are exerted, allowing powering the at least one electrically operated component while moving the electrically operated component using the same wires for moving and powering the component. When the at least one electrically operated component is a camera, these embodiments of the present invention allow using the same wires to power the camera and to change the direction the camera is pointed at. Optionally, one or more electrical signals for controlling the at least one electrically operated component are delivered over cables 103 and 106. For example, when the electrically operated component is a camera, the one or more electrical signals may instruct the camera to change its focal length.

Optionally, cables 103 and 106 deliver one or more electrical signals from the at least one electrically operated component to a receiver attached to cables 103 and 106 at the proximal end of the tubular member. For example, when the at least one electrically operated component is a camera, cables 103 and 106 may deliver multiple electrical signals captured by the camera to a monitor. Optionally, one or more electrical signal modulators are attached to cables 103 and 106 on one side (proximal or distal) and one or more electrical signal demodulators are attached to cables 103 and 106 on an opposite side, for incorporating one or more electrical signals on cables delivering electrical power by modulation of electrical signals on an electrical power line.

Optionally, one or more flexible wires 102 are used to attach cables 103 and 106 to electrically operated component 101, for example when cables 103 and 106 are made of a rigid material or a material that cannot be soldered to inputs of electrical component 101. Flexible wires 102 may be long enough to provide slack to allow tubular member 105 to deform without disrupting the connections between cables 103 and 106 and electrically operated component 101. For example, wires 102 may have a length of at least 3 millimeters. Optionally, wires 102 have a length of 6 millimeters, 7 millimeters, 10 millimeters, 15 millimeters or another length up to 20 millimeters. In embodiments where a first of the one or more cables delivers a plurality of electrical signals from one of the at least one electrically operated components and extends through a first of the one or more lumens, a second of the one or more cables delivers an electrical current to the one of the at least one electrically operated components and extends through a second of the one or more lumens, and a third of the one or more cables delivers an electrical current to another of the at least one electrically operated components and extends through a third of the one or more lumens, the first lumen may be between the second lumen and the third lumen.

Figure 3A:
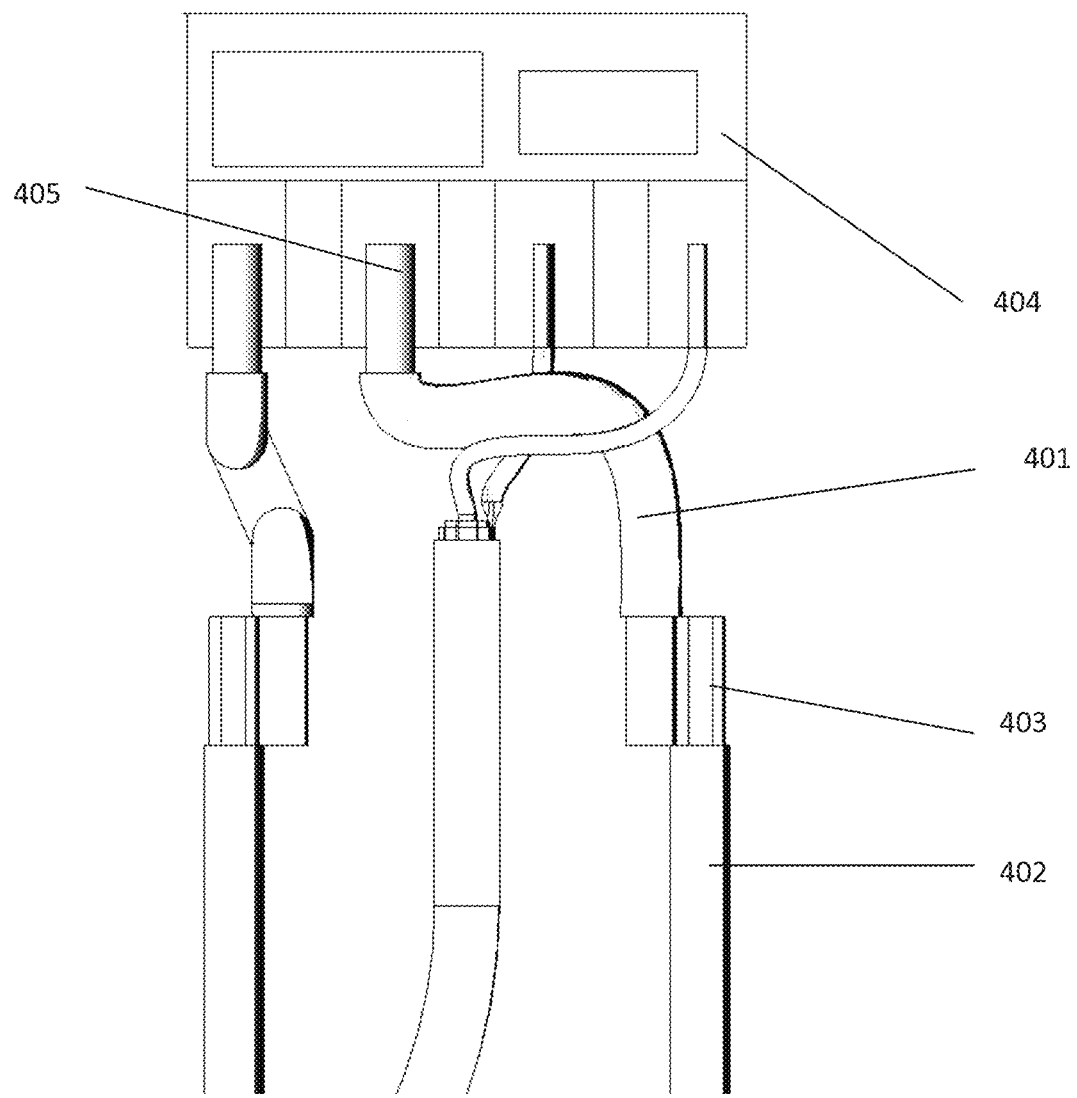
FIGS. 3A and 3B are schematic illustrations of mechanical couplings between a plurality of wires and an electrical component, according to some embodiments of the present invention.
Figure 3B:
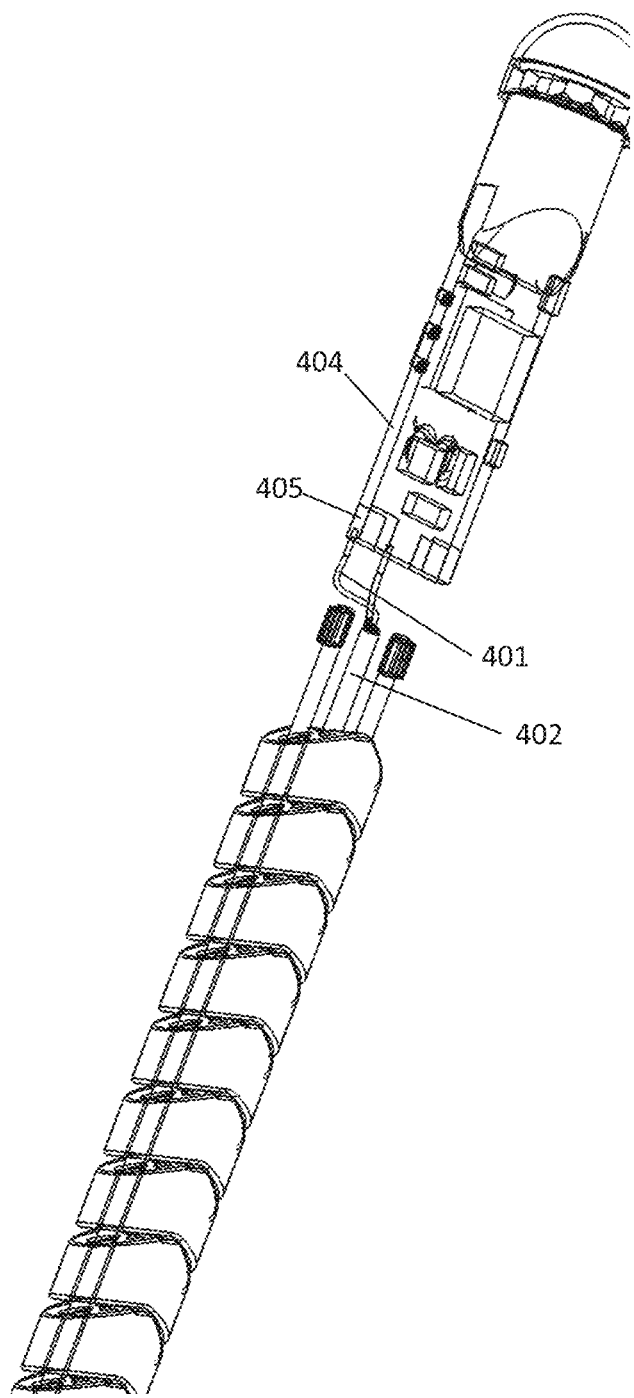

Reference is now also made to FIGS. 3A and 3B, showing schematic illustrations of a mechanical coupling between a plurality of wires and an electrical component, according to some embodiments of the present invention. In some embodiments conductive cable 402 is made of a material, or has a form, not suitable for electrically attaching to an input of electrically operated component 404. In these embodiments, multipurpose conductive cable 402 is mechanically coupled to flexible conductive wire 401 using a crimp connection 403, allowing attaching cables made of different conductive materials in a mechanically secure manner, while maintaining electrical conductivity between cable 402 and wire 401. Optionally, flexible wire 401 is attached at 405 to an input of electrically operated component 404. Flexible wire 401 may be longer than a distance between attachment point 405 and crimp connection 403, providing slack such that attachment point 405 is not disrupted when a force is applied to conductive cable 402.

In some embodiments of the present invention the flexible tubular member has at least one lumen therethrough. Optionally, the flexible tubular member has more than one lumen therethrough.

Figure 4A:
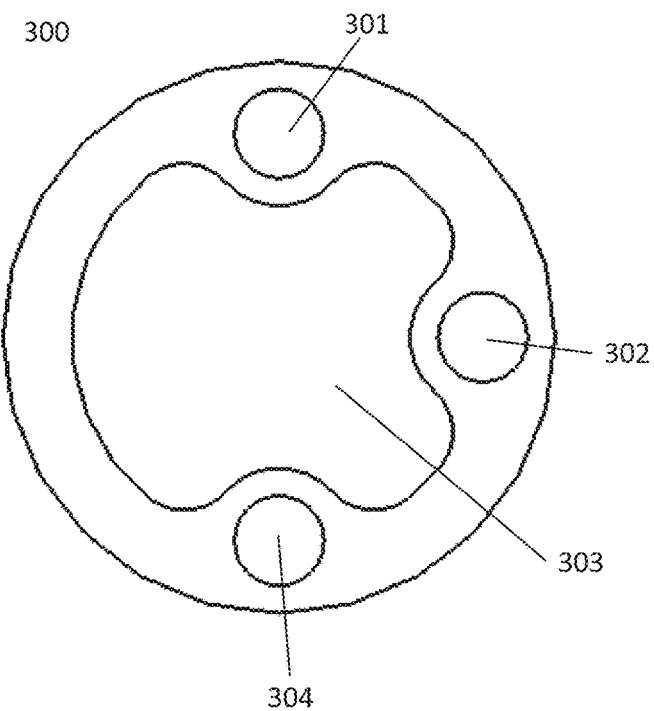
FIGS. 4A and 4B are schematic illustrations of cross sections of possible exemplary multi-lumen members, according to some embodiments of the present invention.
Figure 4B:
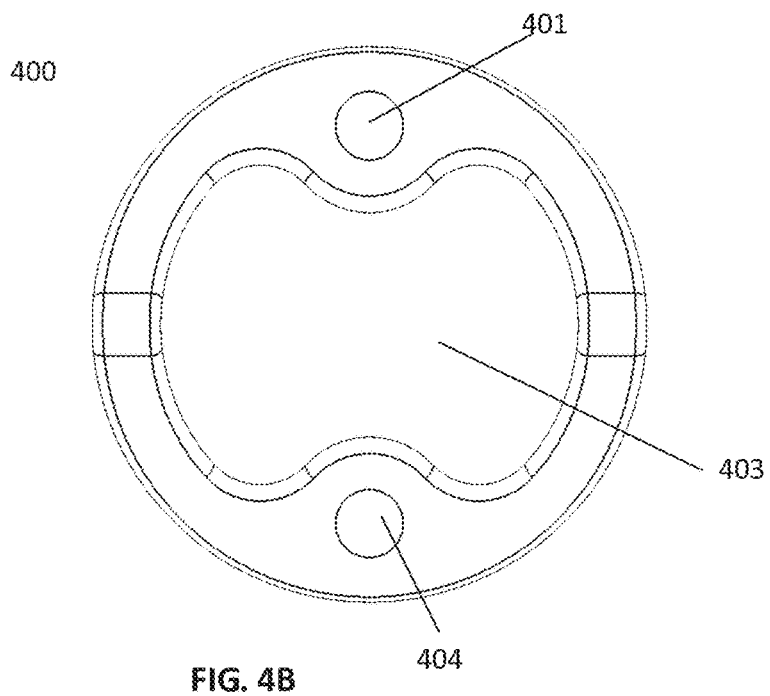

Reference is now also made to FIGS. 4A and 4B, showing schematic illustrations of cross section of possible exemplary multi-lumen members, according to some embodiments of the present invention. In reference to FIG. 4A, in some embodiments, multi-lumen member 300 has a plurality of lumens, for example four lumens 301, 302, 303 and 304. Member 300 may have a diameter of several millimeters, for example 4 millimeters. Optionally, a fluid is transferred through one lumen of the plurality of lumens. Optionally, at least one conductive cable of the one or more conductive cables extends through the one lumen.

Figure 5:
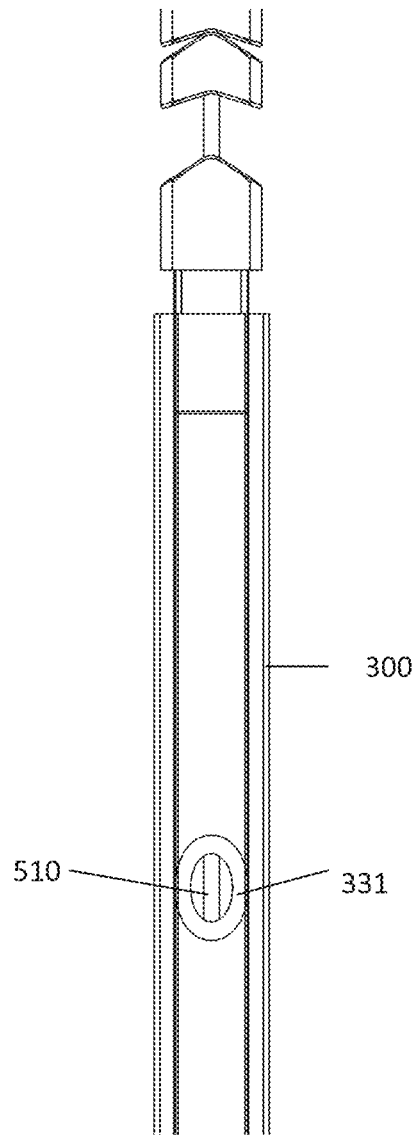
FIG. 5 is a schematic partial illustration of a side view of a distal end of an exemplary catheter, according to some embodiments of the present invention.

Reference is now made also to FIG. 5, showing a schematic partial illustration of a side view of a distal end of an exemplary catheter, according to some embodiments of the present invention. At least one lumen of multi-lumen member 300 has an outlet 331, such that fluid transferred through the at least one lumen from member 300's proximal end to member 300's distal end can exit through outlet 331 into the patient's body. Alternately, fluid may be sucked through outlet 331 from the patient's body by applying suction to member 300's proximal end. Optionally, at least one conductive cable 510 extends through the at least one lumen. Optionally, a cross section of one or more of at least one conductive cable 510 has a diameter of less than 1 millimeter, for example 0.24 millimeters. Optionally, a cross section of the at least one lumen has a diameter less than 1 millimeter, for example 0.65 millimeters.

Reference is now made again to FIG. 4A. Optionally, the at least one conductive cable is coated in an insulating material providing a moisture or dielectric barrier or both, for example parylene p-xylylene, such that a current is driven on the at least one conductive cable while the fluid is transferred through the one lumen. Optionally, the insulating material reduces friction between the at least one conductive cable and the fluid transferred through the one lumen. The fluid may be transferred from the distal end of the tubular member to a proximal end of the tubular member, or from the proximal end of the tubular member to the distal end of the tubular member. Optionally, the one lumen has an outlet at the distal end. In reference to FIG. 4B, in some embodiments, multi-lumen member 400 has another plurality of lumens, for example 3 lumens 401, 403 and 404. In some embodiments where a fluid is transferred through one lumen of the plurality of lumens and at least one conductive cable of the one or more conductive cables extends through the one lumen, at least one of the at least one conductive cables may transfer a plurality of electrical signals to and from the electrically operated component. An example of electrical signals is control signals for controlling the electrically operated component. Another example of electrical signals, when the electrically operated component is a camera, is signals including video images captured by the camera.

In some embodiments, the flexible tubular member comprises a sequence of ring segments having a virtual shaft, providing the flexible tubular member its flexibility.

Figure 6:
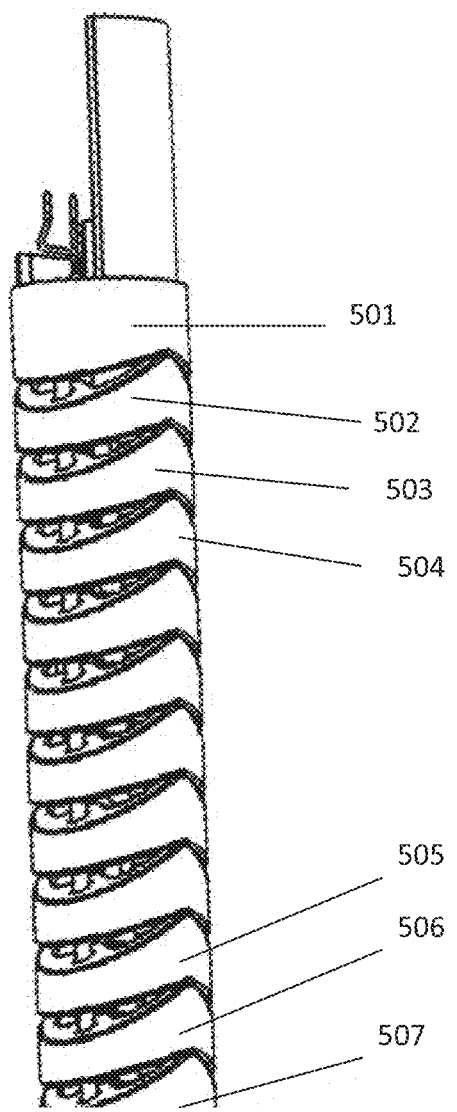
FIG. 6 is a schematic illustration of a side view of a distal end of an exemplary multi-lumen member, according to some embodiments of the present invention.

Reference is now also made to FIG. 6, showing a schematic illustration of a side view of a distal end of an exemplary multi-lumen member, according to some embodiments of the present invention. In such embodiments, the distal end comprises a sequence of ring segments, including ring segments 501, 502, 503, 504, 505, 506 and 507. Optionally, the sequence of ring segments has at least one degree of bending freedom and has a virtual shaft, such that no pins are required for achieving the at least one degree of bending freedom. Optionally, the segments of the sequence of ring segments are made of a polymer, for example Delerin. Each of the sequence of rings optionally has a plurality of lumens. Each of the sequence of ring segments may have a cross section as illustrated in FIG. 4A or FIG. 4B. Optionally, the sequence of ring segments may be encased in an external wrapper, attached to one or more segments of the sequence of ring segments.

Figure 7:
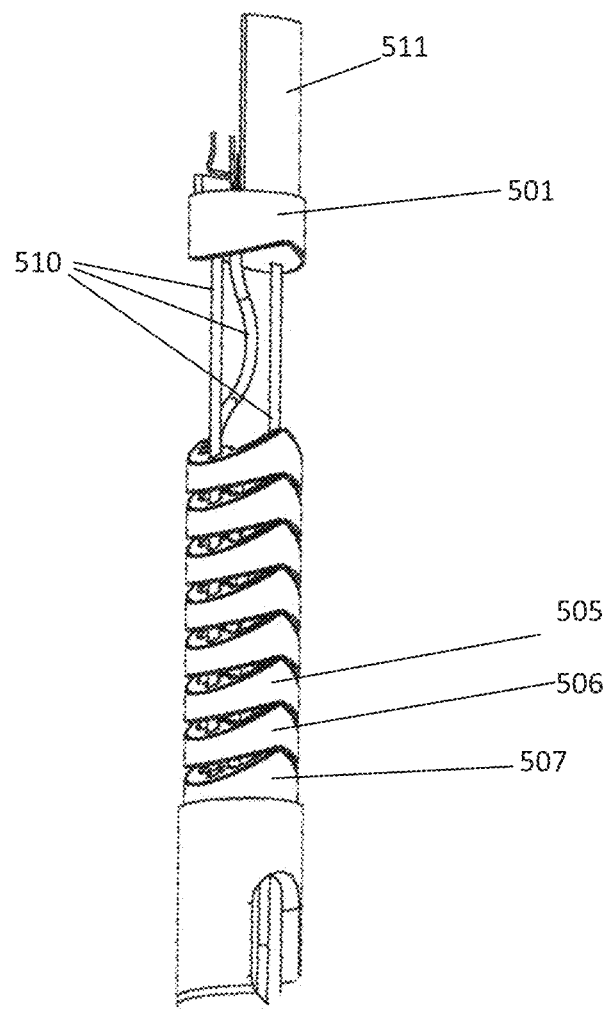
FIGS. 7 and 8 are other schematic illustrations of two side views of the multi-lumen member shown in FIG. 6, without some segments, according to some embodiments of the present invention.
Figure 8:
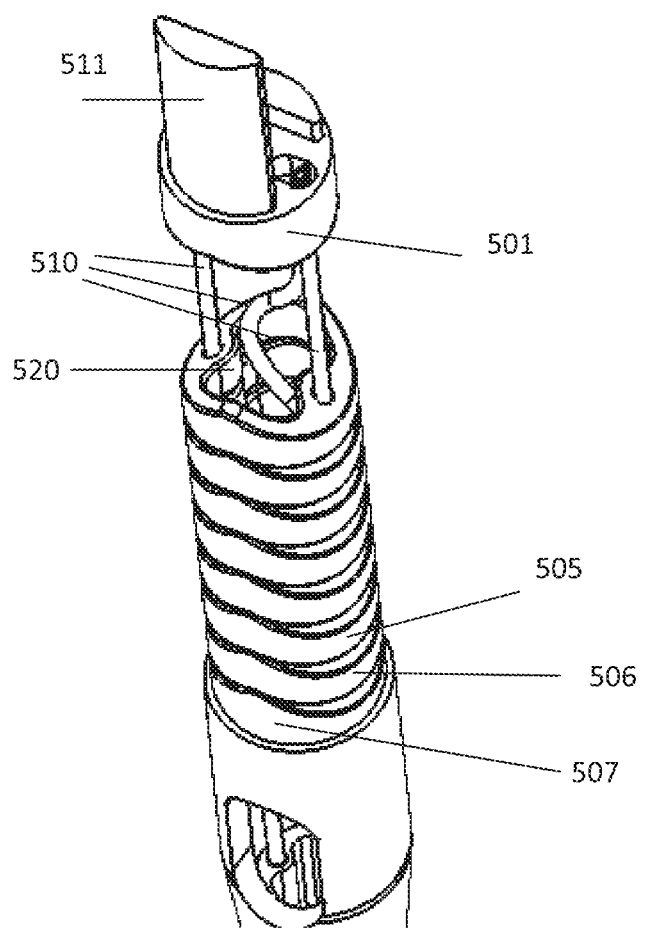

Reference is now also made to FIGS. 7 and 8, showing other schematic illustrations of two side views of the multi-lumen member shown in FIG. 6, without some segments, according to some embodiments of the present invention. In FIGS. 7 and 8, segments 502, 503 and 504 are missing, exposing one or more conductive wires 510 extending through the one or more lumens. Optionally, an electrically operated component 511 is attached to ring segment 501. Some of one or more multipurpose conductive wires 510 may be attached to ring segment 501. Some of the one or more multipurpose conductive wires may be attached to component 511. Optionally, one or more of one or more multipurpose conductive wires 510 extend through lumen 520. A fluid may be transferred through lumen 520 while a current is driven on one or more of the one or more multipurpose conductive wires 510.

In some embodiments of the present invention the distal end of the tubular member is narrower than other parts of the tubular member, to allow delivering the distal end to particularly small organs.

Reference is now also made to FIGS. 9A, 9B and 9C, showing additional schematic illustrations of the multi-lumen member shown in FIGS. 6, 7 and 8, emphasizing a narrowing form, according to some embodiments of the present invention. In such embodiments, ring segment 507 has a diameter narrower than tubular member 300's diameter, and one or more conductive wires 510 are deformed to fit into the narrower diameter. In some embodiments of the present invention, some of the multipurpose conductive wires are hollow, additionally allowing transferring a fluid through some of the multipurpose conductive wires.

In some embodiments of the present invention the distal end of the tubular member is wider than other parts of the tubular member, to allow attaching a larger electrical component at the distal end.

Reference is now also made to FIGS. 10A and 10B, showing additional schematic illustrations of the multi-lumen member shown in FIGS. 6, 7 and 8, emphasizing a widening form, according to some embodiments of the present invention. In such embodiments, ring segment 507 has a diameter wider than tubular member 300's diameter, and one or more conductive wires 510 extend without deformation into the wider diameter. Optionally, one or more conductive wires 510 are deformed to increase a distance between the one or more conductive wires while extending through the wider diameter. Optionally, the distal end further comprises a tube connector 901, formed to have one certain diameter at an end attached to tubular member 300, and another certain diameter, greater than the one certain diameter, at another end attached to ring segment 507.

There are applications using a catheter where inserting the catheter is easier and more accurate when at least two sections of the flexible member may be bent in at least two different bending radii. One example is when inserting a post-pyloric feeding tube, such as inserting the feeding tube into a patient's duodenum. Directing a distal end of the catheter comprising the feeding tube towards the pylorus is easier when the flexible member has a plurality of sections, each section having a bending radius different form another section's bending radius.

Figure 11A:
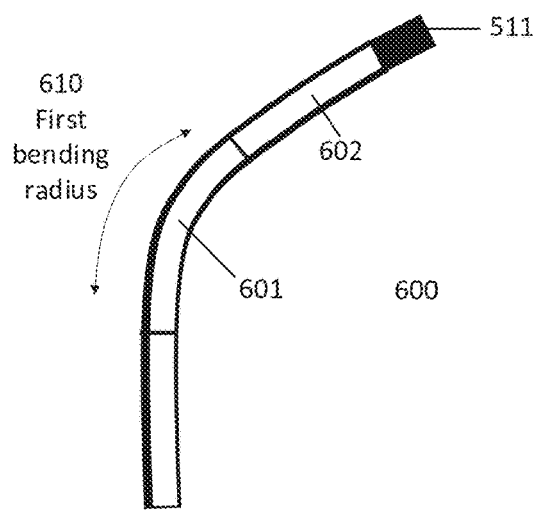
FIGS. 11A and 11B are schematic partial illustrations of an exemplary catheter with a distal end having a plurality of sections with different bending radii, according to some embodiments of the present invention.
Figure 11B:
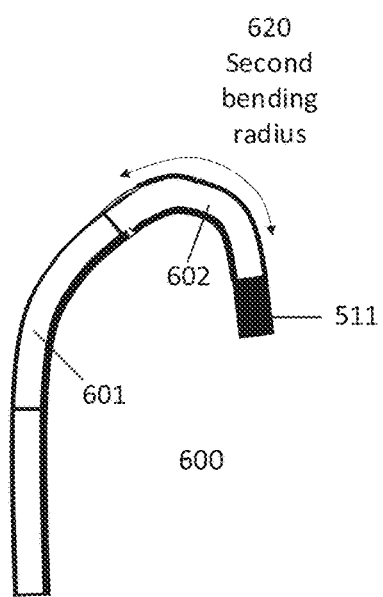

Reference is now made also to FIGS. 11A and 11B, showing schematic illustrations of an exemplary catheter with a distal end having a plurality of sections with different bending radii, according to some embodiments of the present invention.

FIG. 11A shows a distal end of catheter 600, comprising an electrically controlled component 511, and at least two sections 601 and 602, according to some embodiments of the present invention. Section 601 optionally bends at a first bending radius 610 when force is exerted on one or more of the catheter's one or more flexible conductive cables. Reference is now made also to FIG. 11B. Section 602 optionally bends at a second bending radius 620 when force is exerted on the one or more of the catheter's one or more flexible conductive cables. Optionally, bending radius 620 is smaller than bending radius 610, optionally allowing a larger variety of deformations of the flexible member of catheter 600 than when bending radius 610 and bending radius 620 are equal.

Figure 12A:
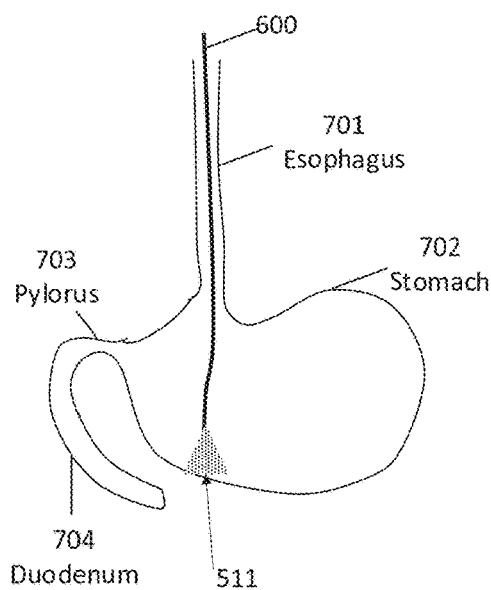
FIGS. 12A, 12B, 12C and 12D are schematic illustrations of possible steps in inserting a post-pyloric feeding tube using, according to some embodiments of the present invention.
Figure 12B:
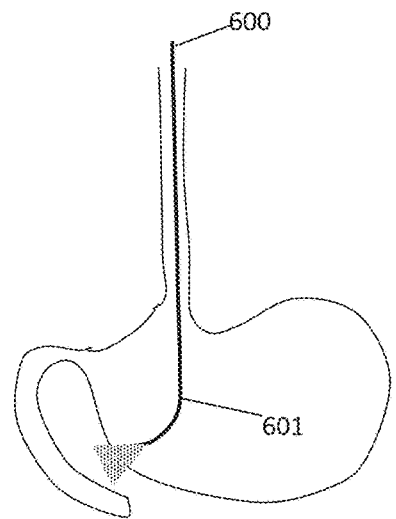
Figure 12C:
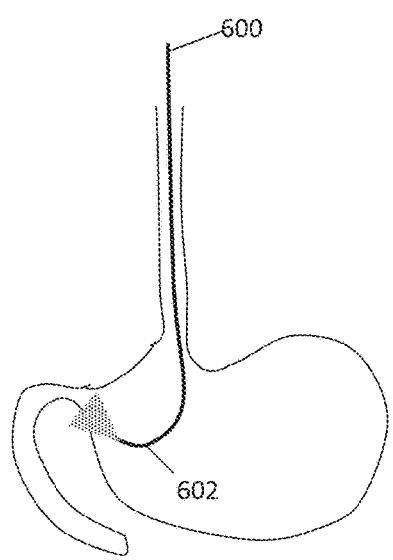
Figure 12D:
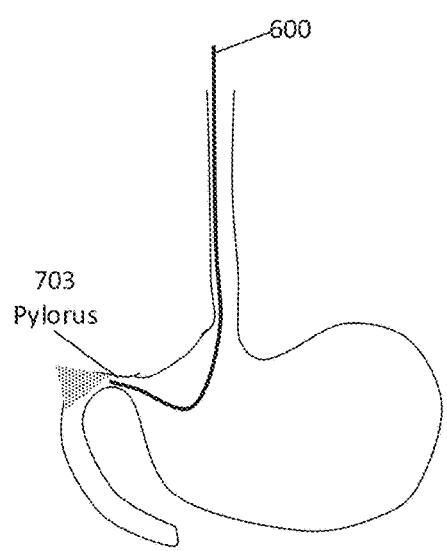

One example where a plurality of bending radii is useful is in insertion of a post-pyloric tube. Reference is now made also to FIGS. 12A, 12B, 12C and 12D, showing schematic illustrations of possible steps in inserting a post-pyloric tube using, according to some embodiments of the present invention. Referring to FIG. 12A, 1n such embodiments, before exerting force on one or more of the one or more flexible conductive cables, catheter 600 comprising electrically controlled component 511 may be inserted straight into a patient's stomach 702 via the patient's esophagus 701, with the purpose of directing the distal end of catheter 600 to duodenum 704 via pylorus 703. Referring now also to FIG. 12B, after some force is exerted on one or more of the one or more flexible conductive cables, section 601 of catheter 600 may bend at a first bending radius. Referring now also to FIG. 12B, after some additional force is exerted on one or more of the one or more flexible conductive cables, section 602 of catheter 600 may bend at a second bending radius. FIG. 12D, demonstrates how after bending a distal end of catheter 600 in more than one bending radius, catheter 600 is optionally directed past pylorus 703.

To achieve a plurality of bending radii in the flexible member, the flexible member may comprise a plurality of sections, where each section has a bending radius different from a radius of another of the plurality of sections.

Figure 13:
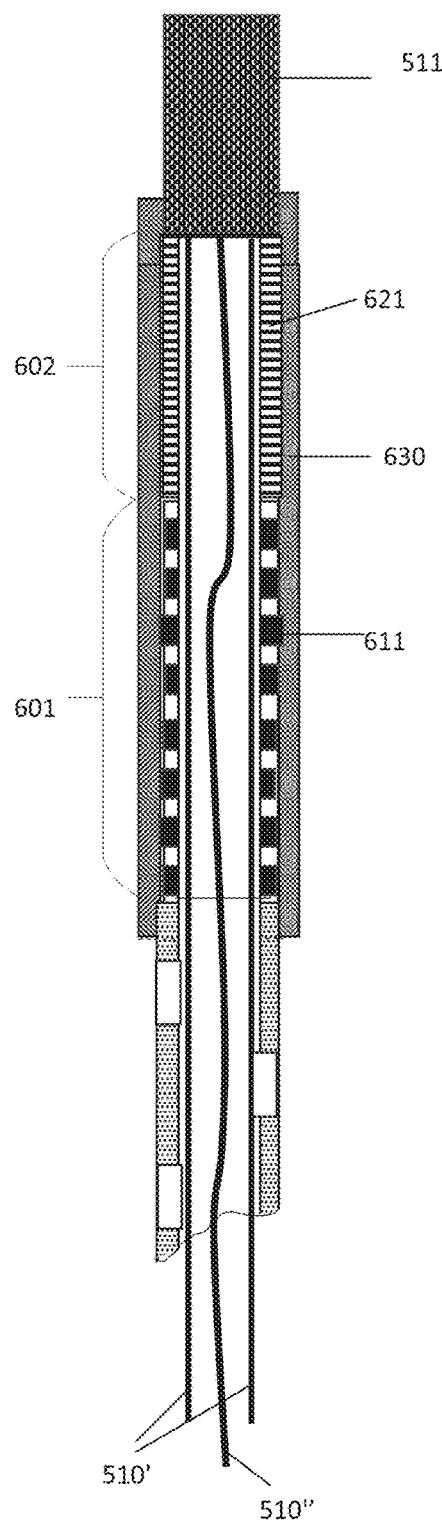
FIG. 13 is a schematic illustration of the plurality of sections shown in FIGS. 11A and 11B, emphasizing segment cylinder heights, according to some embodiments of the present invention.

Reference is now made also to FIG. 13, showing a schematic illustration of the plurality of sections shown in FIGS. 11A and 11B, emphasizing segment heights, according to some embodiments of the present invention. In such embodiments, a flexible member of the catheter comprises an electrically controlled component 511, and one or more flexible conductive cables 510' and 510". Optionally, a sequence of ring segments of the flexible member comprises a plurality of sections 601 and 602, where section 601 is closer to a proximal end of the catheter than section 602. Each of the plurality of sections 601 and 602 comprises a sub sequence of rings, 611 and 621 respectively. A plurality of rings in each sub-sequence of rings optionally has a section ring height.

Figure 14:
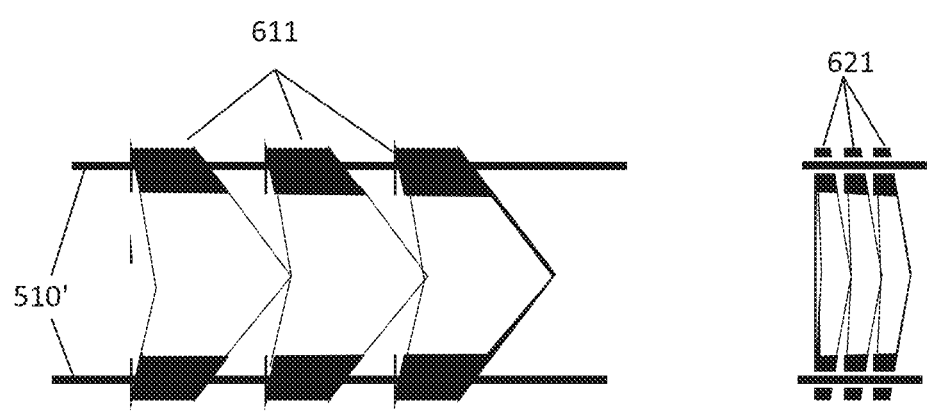
FIG. 14 is a schematic partial illustration of two of the plurality of sections shown in FIG. 13, according to some embodiments of the present invention.

Reference is now made also to FIG. 14, showing a schematic partial illustration of two of the plurality of sections shown in FIG. 13. Sub sequence of rings 611 optionally has a first section ring height. Sub sequence of rings 621 optionally has a second section ring height. Optionally, the first section ring height is greater than the second section ring height. Optionally one or more flexible conductive cables 510' are attached to the sub-sequence of rings 611 and/or sub sequence of rings 621.

Reference is now made again to FIG. 13. When the first section ring height of sub-sequence of rings 611 is greater than the second section ring height of sub-sequence of rings 621, section 601 optionally has a bending radius greater than a bending radius of section 602. Optionally, the plurality of sections comprises more than two sections.

In some embodiments of the present invention, the plurality of rings have a flexible sheath 630. Optionally, sheath 630 is made of a polymer, for example a Silicone polymer.

Friction between one or more of the multipurpose conductive wires and the tubular member may cause some of a force applied to a proximal end of the one or more multipurpose conductive wires to be lost to the tubular member and not be delivered to the distal end of the one or more multipurpose conductive wires.

Figure 15:
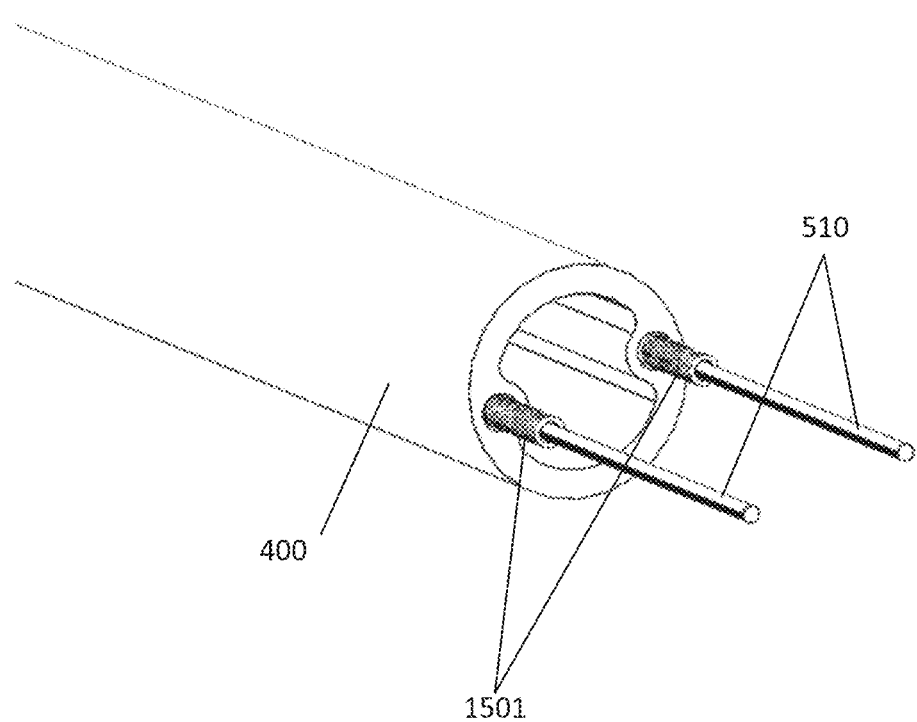
FIG. 15 is a schematic partial illustration of a cross section of an exemplary catheter with a spring sheath, according to some embodiments of the present invention.

Reference is now made also to FIG. 15, showing a schematic partial illustration of a cross section of an exemplary catheter with a spring sheath, according to some embodiments of the present invention. To reduce friction and thus reduce loss of force delivered to the distal end of the one or more multipurpose conductive wires, optionally at least one of the plurality of multipurpose conductive wires 510 is installed inside a spiral tubular cover 1501, or sheath, having a plurality of coils and extending through at least part of at least one lumen of multi lumen tubular member 400. Using a coiled sheath, that is a spring, may reduce friction between the at least one multipurpose conductive wire and the tubular member. Optionally, the spring has a diameter of less than 1 millimeter, for example 0.6 millimeters. Optionally, the spring comprises a wire coiled in a plurality of coils. Optionally the wire has a diameter between 0.05 millimeters and 0.5 millimeters. Optionally, the wire is coiled between 5 and 100 coils per centimeter.

Figure 16:
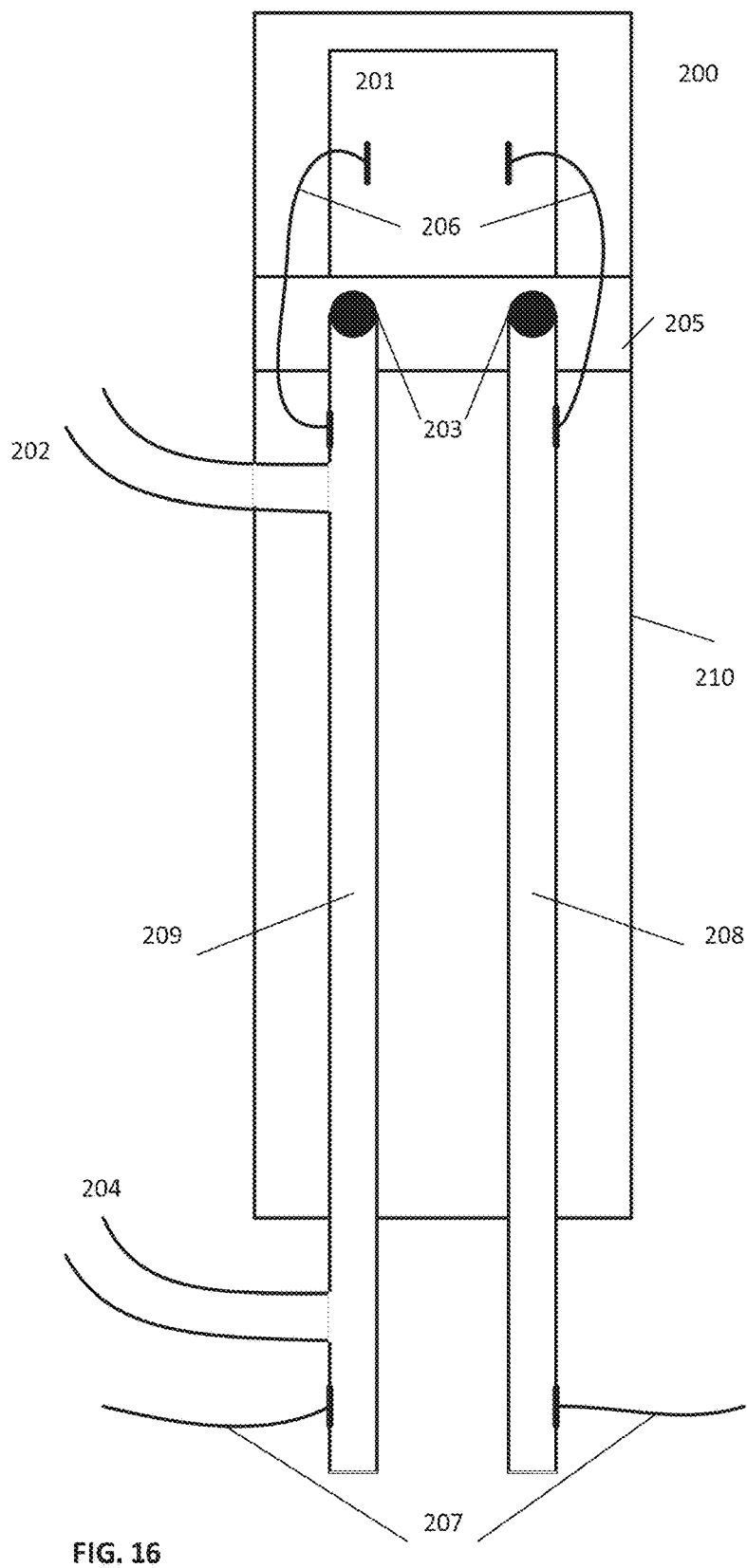
FIG. 16 is a schematic partial illustration of another exemplary catheter according to some embodiments of the present invention, using a common wire for delivering a fluid, a force and an electrical current.

Reference is now also made to FIG. 16, showing a schematic partial illustration of another exemplary catheter 200 according to some embodiments of the present invention, using a common wire for delivering a fluid, a force and an electrical current. In such embodiments, a flexible tubular member 210, having one or more lumens extending therethrough, has an electrically operated component 201 attached at a distal end of the tubular member. Examples of an electrically operated component are a camera and an illumination component. Optionally, flexible tubular member 210 comprises one or more ring segments 205 at the distal end of the tubular member, and has at least one degree of bending freedom. Optionally, the electrically operated component 201 is attached to at least one of ring segments 205, such that movement of the at least one ring moves the electrically operated component. 208 and 209 are one or more hollow multipurpose conductive wires, extending through at least one lumen of flexible tubular member 210, and each having a wire lumen extending therethrough.

One or more hollow multipurpose conductive wires 208 and 209 are optionally mechanically attached to ring segment 205, such that exerting a compressive force on wire 208 and a tensile force on wire 209 move ring segment 205, causing tubular member 210 to tilt and move electrically operated component 201. Wires 208 and 209 may be mechanically attached to ring segment 205 using a mechanical coupling, for example a crimp connection. The mechanical coupling may be reinforced using a bonding agent, for example a high strength epoxy. One or more conductive wires 207 are optionally attached to one or more hollow wires 208 and 209 at a proximal end of tubular member 210, for example for the purpose of connecting one or more wires 208 and 209 to an electrical current source. At the distal end of tubular member 210 one or more flexible conductive wires 206 are optionally connected to one or more hollow wires or capillaries 208 and 209 and to electrically operated component 201, for the purpose of delivering an electrical current to component 201. The at least one electrically operated component may be powered by a direct current (DC) delivered on one of the plurality of multipurpose conductive cables. In addition, in some embodiments one or more electrical signals are delivered on one or more hollow conductive wires 208 and 209 for the purpose of controlling component 201. Optionally, the one or more wire lumens extending through hollow conductive cables 208 and 209 are coated in an insulating material providing a moisture or dielectric barrier or both, for example parylene p-xylylene, such that a fluid may be transferred through one or more hollow conductive cables or capillaries 208 and 209 while delivering at least one electrical current through the one or more hollow conductive cables. This allows using one or more hollow conductive cables 208 and 209 to simultaneously deliver a current for operating electrically operated component 201, deliver at least one force for moving component 201, and transfer a fluid from one end of the tubular member to the other end. Optionally, at least one of the one or more hollow conductive cables 209 has an outlet 202 at the distal end of tubular member 210, enabling delivering a fluid to a location outside the distal end of the tubular member. At least one of the one or more hollow conductive cables 209 has an outlet 204 at a proximal end of tubular member 210, for the purpose of delivering a fluid into one or more hollow conductive cables 209.

Optionally, the one or more ring segments 205 are a sequence of ring segments having a virtual shaft, such that no pins are required for achieving the at least one degree of bending freedom. In some embodiments, one or more hollow conductive cables 208 and 209 are attached at the proximal end of tubular member 210 to a pulley or capstan, and a motion of the pulley or capstan exerts the tensile force and compressive force on cables 208 and 209.

Electrically operated component 201 may be mounted at member 210's distal end on a printed circuit board (PCB) having one or more fixing elements, for example a crimp connection or nuts and bolts, and the one or more multipurpose conductive cables may be attached to member 210 using the PCB's fixing elements. In some embodiments the PCB has an elongated form, fitting in the distal end of tubular member 210.

In embodiments where a first of the one or more cables delivers a plurality of electrical signals from one of the at least one electrically operated components and extends through a first of the one or more lumens, a second of the one or more cables delivers an electrical current to the one of the at least one electrically operated components and extends through a second of the one or more lumens, and a third of the one or more cables delivers an electrical current to another of the at least one electrically operated components and extends through a third of the one or more lumens, the first lumen may be between the second lumen and the third lumen.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant flexible tubular members, mechanical couplings and electrical components will be developed and the scope of the terms "flexible tubular member", "mechanical coupling" and "electrical component" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A catheter, comprising:
 a flexible tubular member having at least one lumen therethrough and a proximal end and a distal end;
 a plurality of conductive cables extending through at least one of said at least one lumen; and at least one electrically operated component, attached at said distal end and powered by at least one electrical current driven on at least one of said plurality of conductive cables;

wherein some of said plurality of conductive cables are attached to said distal end such that said flexible tubular member is deformed by exerting at said proximal end a tensile force on one of said some of said plurality of conductive cables and a compressive force on another of said some of said plurality of conductive cables, while said at least one electrical current is driven on said some of said plurality of conductive cables;

wherein said some of said plurality of conductive cables are attached to a terminal segment of the flexible tubular member configured at said distal end by a mechanical coupling selected from a group consisting of a crimp connection, a welding, a bonding and a soldering;

wherein said some of said plurality of conductive cables are electrically attached to said at least one electrically operated component using at least one length of flexible conducting wire extending from the mechanical coupling at the terminal segment to an electrical input of the at least one electrically operated component; and wherein the at least one length of flexible conducting wire provides slack to allow adjustment of an orientation of at least one electrically operated component through adjustment of orientation of the terminal segment, without disrupting the electrical coupling between said some of said plurality of conductive cables and said electrical input.

2. The catheter of claim 1, wherein said at least one of said plurality of conductive cables is coated in an insulating material such that said electrically operated component is powered by said at least one electrical current while a fluid is transferred through said at least one lumen.

3. The catheter of claim 2, wherein said at least one lumen has an outlet at said distal end.

4. The catheter of claim 1, wherein said at least one electrically operated component comprises a camera or an illumination component.

5. The catheter of claim 4, wherein said illumination component is a light emitting diode in the ultra-violet, visible or infra-red spectrum (VLED), powered by said at least one electrical current.

6. The catheter of claim 1, wherein said flexible tubular member comprises at said distal end a sequence of ring segments having a virtual shaft, such that said flexible tubular member has at least one degree of bending freedom.

7. The catheter of claim 6, wherein said sequence of ring segments comprises a plurality of sections, each comprising a sub-sequence of rings, each ring having a certain section ring height;

wherein a first section is closer to a proximal end of said flexible tubular member than a second section; and wherein a first section ring height of said sub-sequence of rings of said first section is greater than a second ring height of said sub-sequence of rings of said second section, such that a bending radius of said first section is greater than a bending radius of said second section.

8. The catheter of claim 7, wherein said sequence of ring segments comprises two sections;

wherein said first ring height is greater than 2 millimeters and up to 5 millimeters; and wherein said second ring height is less than 2 millimeters.

9. The catheter of claim 6, wherein the ring segments in the sequence of ring segments are held in place around the plurality of conductive cables based only on tensile or compressive preload forces on the plurality of conductive cables, without any pins or rivets connecting adjacent ring segments.

10. The catheter of claim 6, wherein the flexible tubular member is movable in the at least one degree of bending freedom based only on application of tensile or compressive forces on one or more of the plurality of conductive cables, without use of pins or rivets connecting adjacent ring segments.

11. The catheter of claim 1, wherein at least one of said plurality of conductive cables is installed in a spiral tubular member having a plurality of coils;

wherein said spiral tubular member extends through at least part of one of said at least one lumen, wherein the spiral tubular member reduces friction between said at least one of said plurality of conductive cables and the at least one lumen when tensile force is exerted on said at least one of said plurality of conductive cables.

12. The catheter of claim 1, wherein said spiral tubular member comprises a wire having a diameter between 0.05 millimeters and 0.5 millimeters; and wherein said wire is coiled between 5 and 100 coils per centimeter.

13. The catheter of claim 1, wherein said at least one length of flexible conducting wire has a length of between 3 and 20 millimeters.

14. The catheter of claim 1, wherein said mechanical coupling is reinforced by a bonding agent at one or more points of contact between said plurality of conductive cables and said flexible tubular member.

15. The catheter of claim 1, further comprising at said distal end of said flexible tubular member a sequence of ring segments having a virtual shaft; and wherein said mechanical coupling is between said plurality of conductive cables and at least one ring segment of said sequence of ring segments.

16. The catheter of claim 15, wherein a diameter of at least one of said sequence of ring segments is narrower than a diameter of said flexible tubular member at a proximal end of said flexible tubular member.

17. The catheter of claim 15, wherein a diameter of at least one of said sequence of ring segments is wider than a diameter of said flexible tubular member at a proximal end of said flexible tubular member.

18. The catheter of claim 1, further comprising a pulley or capstan at said proximal side;

wherein said some of said plurality of conductive cables are connected to said pulley or capstan, such that a motion of said pulley or capstan exerts at said proximal end a tensile force on at least one of said some of said plurality of conductive cables and a compressive force on at least one other of said some of said plurality of conductive cables.

19. The catheter of claim 1, wherein at least one of said at least one electrical current is either a direct current (DC) or an alternating current (AC).

20. The catheter of claim 1, wherein at least one first of said plurality of conductive cables delivers a plurality of electrical signals from said at least one electrically operated component to a receiver electrically attached to said at least one of said plurality of conductive cables;

wherein said at least one first conductive cable extends through a first of said at least one lumen;

wherein at least one second of said plurality of conductive cables delivers an electrical current to a first of said at least one electrically operated component and extends through a second of said at least one lumen;

wherein at least one third of said plurality of conductive cables delivers an electrical current to a second of said at least one electrically operated component and extends through a third of said at least one lumen; and wherein said first lumen is between said second lumen and said third lumen.

21. The catheter of claim 1, wherein said at least one electrically operated component comprises a printed circuit board (PCB), said PCB having an elongated form, fitting inside said flexible tubular member.

22. A catheter, comprising:
a flexible tubular member having at least one lumen therethrough and a proximal end and a distal end;
a plurality of hollow conductive cables, extending through said at least one lumen and each having a cable lumen therethrough; and
at least one electrically operated component, attached at said distal end and powered by at least one electrical current driven on at least one of said plurality of hollow conductive cables;
wherein said cable lumen is coated in an insulating material such that said electrically operated component is powered by said at least one electrical current while a fluid is transferred through said cable lumen of said at least one of said plurality of hollow conductive cables.

23. The catheter of claim 22, wherein said cable lumen has an outlet at said distal end.

24. The catheter of claim 22, wherein some of said plurality of hollow conductive cables are attached to said distal end such that said flexible tubular member is deformed by exerting at said proximal end a tensile force on one of said some of said plurality of hollow conductive cables and a compressive force on another of said some of said plurality of hollow conductive cables, while said fluid is transferred through said cable lumen.

\* \* \* \* \*